US010271918B2

United States Patent
Chow et al.

(10) Patent No.: US 10,271,918 B2
(45) Date of Patent: Apr. 30, 2019

(54) MEDICAL DEVICE MANAGEMENT UNIT

(71) Applicant: Ken Wah Chow, Davis, CA (US)

(72) Inventors: Ken Wah Chow, Davis, CA (US);
Kenneth William Chow, Davis, CA (US); Jack Krzyzanowski, Mississauga (CA)

(*) Notice: Subject to any disclaimer, the term of this patent is extended or adjusted under 35 U.S.C. 154(b) by 0 days.

(21) Appl. No.: 15/052,141

(22) Filed: Feb. 24, 2016

(65) Prior Publication Data

US 2016/0242862 A1 Aug. 25, 2016

Related U.S. Application Data

(63) Continuation-in-part of application No. 14/628,605, filed on Feb. 23, 2015, now abandoned.

(51) Int. Cl.
| | |
|---|---|
| *A45F 3/14* | (2006.01) |
| *A61B 50/22* | (2016.01) |
| *A61B 17/06* | (2006.01) |
| *A61M 25/02* | (2006.01) |
| *A61B 50/20* | (2016.01) |
| *A61B 50/30* | (2016.01) |
| *A61B 17/00* | (2006.01) |

(52) U.S. Cl.
CPC ........ *A61B 50/22* (2016.02); *A61B 17/06061* (2013.01); *A61B 50/20* (2016.02); *A61M 25/02* (2013.01); *A61B 2017/0042* (2013.01); *A61B 2017/00438* (2013.01); *A61B 2050/3008* (2016.02); *A61M 2025/0213* (2013.01)

(58) Field of Classification Search
CPC ... A61B 17/06061; A61B 50/20; A61B 50/22; A61B 2017/0042; A61B 2017/00438; A61B 2050/3008; A61B 19/0256; A61M 25/02; A61M 2050/0206; A61M 2050/024
USPC .................................................. 224/217, 218
See application file for complete search history.

(56) References Cited

U.S. PATENT DOCUMENTS

| | | | | |
|---|---|---|---|---|
| 5,242,458 | A * | 9/1993 | Bendel ............... | A61B 17/0469 606/147 |
| 5,319,837 | A * | 6/1994 | Kujawski ............. | F16L 3/2235 24/16 R |
| 5,617,952 | A * | 4/1997 | Kranendonk ........ | A61B 17/062 206/380 |
| 6,227,502 | B1 * | 5/2001 | Derman ................ | F16L 3/2235 248/68.1 |
| 8,480,690 | B2 * | 7/2013 | Vijayanagar ..... | A61B 17/06061 24/598.2 |
| 8,517,233 | B2 * | 8/2013 | Podda-Heubach .... | A61B 90/53 224/183 |
| 8,856,963 | B2 * | 10/2014 | Nagda ................. | A41D 13/087 2/21 |

(Continued)

FOREIGN PATENT DOCUMENTS

WO WO-2014113702 A1 * 7/2014 ............... F16L 3/23

*Primary Examiner* — Nathan J Newhouse
*Assistant Examiner* — Lester L Vanterpool

(57) ABSTRACT

The present invention relates to medical device management units and methods of their use. The medical device management units comprise two main pieces, a base piece, and a slide piece, as well as at least one medical device pathway defined by a surface means and a plurality of trenches. The invention may be used to keep two or more medical devices organized or it may be used to maintain control over the capture and release of a single medical device.

22 Claims, 11 Drawing Sheets

(56) References Cited

U.S. PATENT DOCUMENTS

| | | | | |
|---|---|---|---|---|
| 8,974,421 B1* | 3/2015 | Khalaj | ................ | A61M 25/02<br>604/174 |
| 9,084,593 B2* | 7/2015 | Yakel | ................ | A61B 19/0271 |
| 2006/0226032 A1* | 10/2006 | Zalsman | ................ | A45C 11/00<br>206/63.5 |
| 2009/0005794 A1* | 1/2009 | Lowry | ................ | A61B 17/0206<br>606/148 |
| 2011/0152893 A1* | 6/2011 | Vijayanagar | ..... | A61B 17/06061<br>606/148 |
| 2011/0152894 A1* | 6/2011 | Vijayanagar | ..... | A61B 17/06061<br>606/150 |
| 2012/0289975 A1* | 11/2012 | Martin | ................ | A61B 17/062<br>606/147 |
| 2013/0079722 A1* | 3/2013 | Makino | ................ | A61M 25/02<br>604/174 |
| 2013/0165863 A1* | 6/2013 | Nilson | ................ | A61M 25/02<br>604/180 |
| 2014/0025010 A1* | 1/2014 | Stroup | ................ | A61M 25/02<br>604/179 |
| 2014/0213980 A1* | 7/2014 | Filippelli | ................ | A61M 25/02<br>604/179 |
| 2015/0141962 A1* | 5/2015 | Collins | ................ | A61M 25/02<br>604/513 |
| 2015/0157829 A1* | 6/2015 | Bunch | ................ | A61M 25/02<br>604/174 |

* cited by examiner

MEDICAL DEVICE MANAGEMENT UNIT

FIELD OF THE INVENTION

This invention relates to a medical device management unit for organizing one or more medical devices.

BACKGROUND OF THE INVENTION

Many types of medical and surgical procedures such as gastroenterology (during endoscopic retrograde cholangiopancreatography (ERCPs), esophagogastroduodenoscopy (EGDs) and colonoscopies), cardiology (cardiac catheterizations), and interventional radiology, employ the use of cables, sutures, catheters, guidewires, balloons, rods or other medical devices during a single procedure. For such procedures it is traditional for medical assistants to supply the physician with the correct medical device at the appropriate time during the course of the procedure. Commonly, the handling of medical devices during the procedures is frustrating and burdensome because these devices can easily become tangled, and the medical devices that appear to be the same may be misplaced when they are of similar gauge, type, and/or length.

Although some medical devices can be dispensed from a traditional spool or circular coil container during the course of a procedure, it is often times desirable to have the medical devices precut to their desired length to minimize both the time of procedure and the risk of measurement error. For example, in procedures where sutures are used, the precut sutures are typically set in the contours of a folded or pleated towel. An inadvertent tug or jolt to the surface the towel is arranged on may ruffle or displace the folded or pleated towel portions, leading to wasted time and frustration. Often times when the towel is jostled the sutures will become tangled, knotted, and/or stuck together, which can be extremely problematic if sutures of various types or gauges are being utilized.

Certain devices have been designed with various degree of success in the art to address the problems inherent in keeping medical devices organized and readily available during medical procedures as previously described. For example, many of these devices require medical staff and surgical assistants to use clips resembling a clothes pin to manage the array of medical devices. However, the existing clips do not allow sequential capture and release of these accessories, which often leads to a tangled mess and additional frustration. Designs that have attempted to solve the inherent problems associated with managing medical devices and similar counterparts are provided below.

U.S. Pat. No. 6,458,104 to Gautsche relates to a device for organizing and securing several IV lines together, and more particularly, to a device for organizing, securing and identifying a plurality of IV tubes in conjunction with an exterior structure. The device has a hollow cylindrical fastening member upon which a plurality of tube holding members of cylindrical bore are arranged. Each of the tube holding members is oriented perpendicularly to the fastening member's longitudinal cylindrical axis and has a full length longitudinal slit aperture opposite the fastening member, with the slit aperture accessing the holding member cylindrical bore. However, Gautsche's invention is larger than would be practical for use as a handheld surgery tool and it does not provide a means for controlled release of tubing, wires, or other surgical components.

U.S. Pat. No. 3,819,039 to Erickson relates to holding devices for retaining multiple surgical sutures. The suture holder utilizes a block or walled configuration constructed from a resilient material and a plurality of abutments defined by slits formed in the block. The abutments are aligned parallel with one another and are arranged so that opposing faces of side-by-side abutments contact one another with gentle pressure. Surgical sutures are positioned within the slits and held steady in desired positions by the opposing faces of abutments associated with the slits. Erickson's invention is also too large to be easily manipulated in a handheld fashion and it would be impractical for controlling the release of a single medical line due to its size. Furthermore, sutures of the same type can still easily become tangled and stuck together when they are placed in common slits of the device as illustrated in the disclosure.

U.S. Pat. No. 4,084,692 to Bilweis describes a surgical thread dispenser having a ring-like structure so that it can be worn on the finger of a physician during surgical procedures. The surgical thread dispenser has a flat, cylindrical reel for holding a surgical thread wound thereon, a case for said reel enclosing the reel on one side and around the outer periphery thereof with an opening in the peripheral rim of the case through which the tread is dispensed from the reel, and a split finger ring affixed to the reel case through an arcuate membrane which enables the practitioner to hold the reel case in the palm of his hand while his fingers remain unencumbered. Bilweis's device is limited to dispensing surgical string, and it does not provide the ability to simultaneously control multiple medical lines.

U.S. Pat. No. 5,562,732 to Eisenberg discloses a hair graft support tray supported on a ring structure to be worn by a physician during hair transplant procedures. The tray has a plurality of receptors for supporting tissue grafts and a plurality of parallel grooves, each of which has at least one drainage hole. The tray is mounted to a support with a set of mounting grooves such that it can slidably detach from the support. Eisenberg's device, while handhold and portable, is directed to the field of hair grafting. The device does not aid in the management of medical devices such as cables, sutures, catheters, wires, balloons, or rods.

U.S. Pat. No. 4,901,847 to Kesling relates to the field of orthodontics and teaches an elastic ligature dispenser for use by an orthodontist when desiring to apply one or more ligatures to an orthodontic system on a patient. A plurality of ligatures are secured to a support member, the support member being connected to a ring structure so as to provide quick and easy access to the ligatures when necessary. Kesling's apparatus is directed to the orthodontics field and is not useful for medical line management or organization.

U.S. Pat. App. 2007/0193903 to Opie et al. teaches a circular, medical guide wire containment/dispenser system. The circular body contains one or more spiral grooves closed by a matching, clip-on lid and there are preferably lateral and medial ramps or bumps on both sides of the spirals, which deflect the wires toward the center of the spiral. The deflection of the wires from the sides of the body reduces friction allowing for more efficient wire extraction. The Opie device is limited to guide wires and would be much too large and cumbersome to use as a handheld piece for managing medical devices.

U.S. Pat. No. 5,915,560 to George et al. discloses a compartmentalized pill dispenser having a protective outer sheath and an internal pill carrier within the sheath. The pill carrier has a detent mechanism capable of releasably stopping the sheath in relation to the pill carrier after each sequential pill cavity has been uncovered. The pill carrier is designed to dispense one pill at a time and can be colorized or color coded to designate the type of medication contained therein. George et al. discloses a unique dispensing mechanism. However, it is limited to carrying and dispensing pills and would be of no use in medical line management.

U.S. Pat. No. 2,893,548 to Carver et al. discloses a surgical ligature dispenser having a cylindrical casing, having two open ends enclosing a spindle, wherein a suture reel is fitted onto the spindle and dispenser. A ligature is fed through the side opened slot of the casing that anchors the spindle with the first opened end of the casing, while the spindle has a flange on one end and a beveled collar on the other end that fits through the second opened end of the casing and is snapped tight. Carver's dispenser is limited to a specific sized ligature of limited quantities, and can be rendered inoperable when the ligature becomes loose and jams the spindle within the casing.

U.S. Pat. No. 8,480,690 to Vigayangar discloses a suture organizer to maintain a plurality of sutures attached to a patient during a surgical procedure, comprising a hemostat retainer to receive and retain the finger hole, and a clasp to clamp a surgical drape to hold the suture organizer in position during operation. Vigayangar's device offers no means to secure wires or sutures within the organizer. Thus, sutures or catheters will most likely be entangled. Further, the device is placed in close proximity to drapes, posing contamination risk for the sterilized sutures or wires.

Thus, there is a need for a small, easy to use, hand-held medical device management unit which is capable of securing, making readily available, and maintaining control over capture and release of one or more medical devices.

SUMMARY OF THE INVENTION

The present invention relates to a medical device management unit for keeping one or more medical devices organized during a medical procedure, as well as maintaining control over the one or more medical devices during its release or capture.

A medical device management unit comprising, a base piece and a slide piece, the base piece comprising 1) a surface means for at least one cables, sutures, catheters, balloons, rods, and/or guide wires to rest upon, and a plurality of trenches spaced apart on the surface means or along the length of the surface means, wherein the trenches define at least one medical device pathway. The slide piece comprises a first end and a second opposing end. The slide piece is operatively slideable over the surface means to secure the at least one medical device within the at least one medical device pathway. The device allows a user to maintain control over cables, sutures, catheters, balloons, rods, and/or guidewires during their release or capture, as well as organized them from entanglement.

BRIEF DESCRIPTION OF THE DRAWINGS

The invention, together with the other objects, features, aspects and advantages thereof will be more clearly understood from the following in conjunction with the accompanying drawings.

DETAILED DESCRIPTION OF THE INVENTION

The present invention relates to a medical device management unit for keeping one or more medical device organized during a medical procedure as well as maintaining control over the one or more medical device during its release or capture.

A medical device management unit comprising, a base piece and a slide piece, the base piece comprising a surface means for at least one cables, sutures, catheters, balloons, rods, and/or guide wires to rest upon, and a plurality of trenches spaced apart on the surface means or along the length of the surface means, wherein the trenches define at least one medical device pathway. The slide piece comprises a first end and a second opposing end, and is operatively slideable over the surface means with or without a cover means, to secure the at least one cables, sutures, catheters, balloons, rods, and guide wires within the at least one medical device pathway. The device allows a user to maintain control over cables, sutures, catheters, balloons, rods, and/or guide wires during their release or capture, as well as organized them.

The base piece of the management unit further includes a first side and an opposing second side, and optionally, a channel that is beneath the surface means, and is preferably parallel with the first side, and the opposing second side.

If the channel is present, the slide piece further includes a locking means that slides into the channel of the base piece to secure the slide piece with the base piece to form the management unit in a "locked" position to hold cables, sutures, catheters, balloons, rods, and/or guide wires. The locking means may be connected to the cover means of the slide piece via a connecting means, such that when the cover means slides over and covers the surface means, the locking means slides into the channel simultaneously or sequentially with minimal delay.

Figure 8:
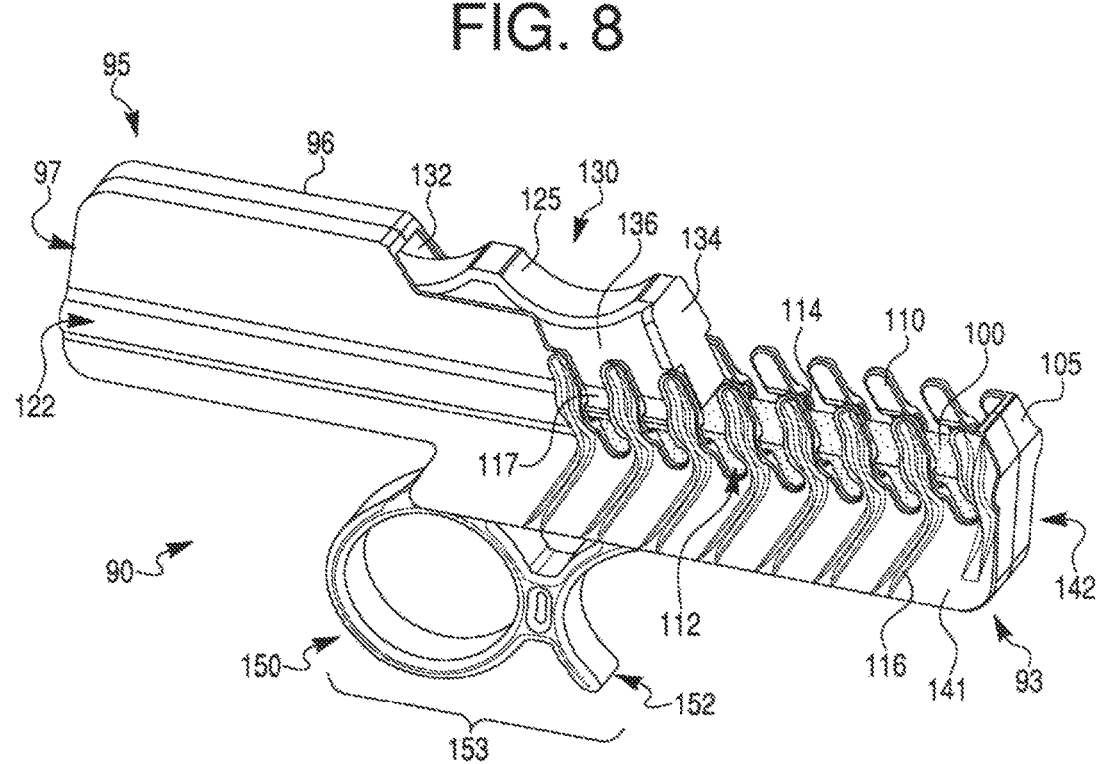
FIG. 8 depicts a side view of an alternative embodiment of the medical device management unit having a slide piece that retracts into a base piece to expose the surface means, forming an "open" position.
Figure 9:
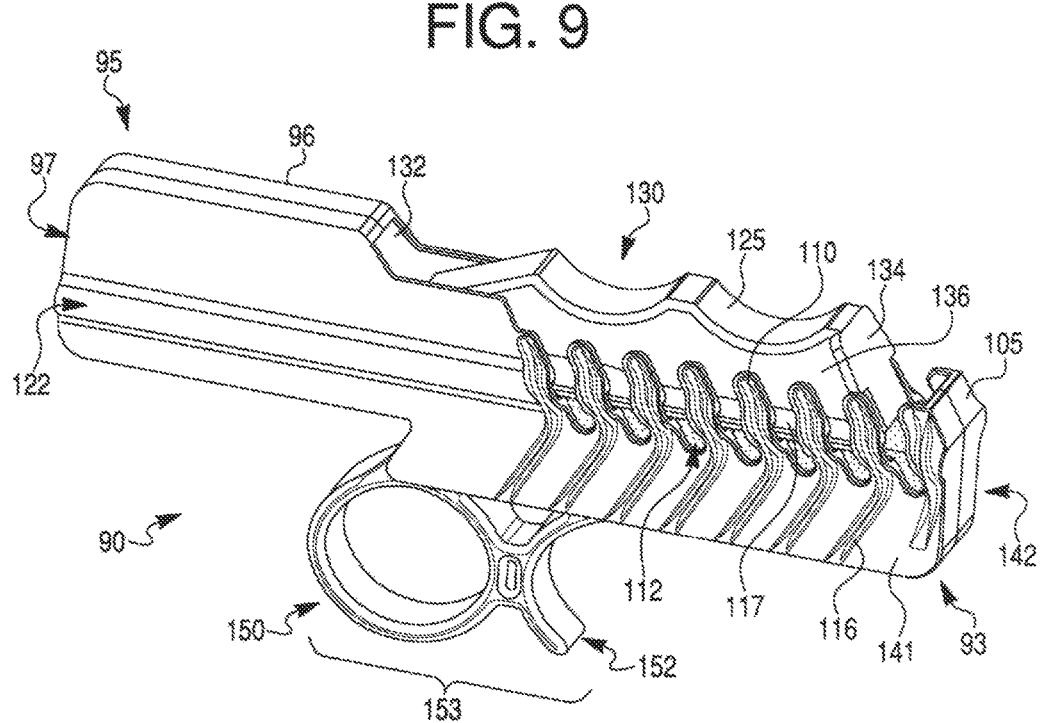
FIG. 9 depicts a side view of an alternative embodiment of the medical device management unit having a slide piece that covers most of the surface means, forming a "closed" position.

In another embodiment, the slide piece includes an anchoring means, wherein the anchoring means secures the slide piece within or onto the base piece, such that upon force exerted onto the slide piece, it slides over to cover the surface means in a locked position to hold cables, sutures, catheters, balloons, rods, and/or guide wires. The anchoring means engages a capture means located on or within the base piece, such that when the slide piece is still, it is captured or anchored via the capture means, and yet with force exerts onto the slide piece, the anchoring means can be flexed and released from the capture means to allow the slide piece to move, forming either "open" or "closed" positions over the surface means as shown in FIGS. 8 and 9.

The base piece further includes a support means or a plurality of protrusions and raises above the surface means along the first and opposing second side of the surface means. The surface means or protrusions form trenches along the length of the surface means. The cover means or slide piece is slideable over either or both of the central portion and the support means of the surface means.

The present invention is useful in keeping cables, sutures, catheters, balloons, rods, and/or guide wires and other medical devices off of the floor and in maintaining sterility. The device also allows the assistant to maintain an orderly working field, thereby allowing the assistant to quickly hand over a needed accessory to the physician performing the procedures.

While the invention is capable of many embodiments, certain preferred embodiments of a medical device management unit are set forth in detail.

The medical devices that may be managed and organized by the medical unit of the present invention include, without limitation, cables, sutures, catheters, balloons, rods, and guidewires.

FIGS. 1, 2A, 2B, 3, 4, and 5 reflect one embodiment of the invention wherein the medical device management unit 1 has a base piece 5 and a slide piece 10. One or more medical device 65 may be organized and managed by placing the cover means 15 over the surface means 25, and locking the medical device 65 into trenches 60. The surface means 25 and the cover means 15 may be flat as shown in FIGS. 1, 2A, 2B, 3, and 4, or they may be dome shaped as demonstrated by FIG. 5. A locking means 30 engages a channel 40, such that the engagement enables a connecting means 35 to motion the cover means 15 to slide over and to cover the support means 20 that is located on first side 3 and opposing second side 8. The locking means 30 comprises at least one protrusion 45, and the channel 40 comprises at least one notch 50 such that the at least one protrusion 45 engages the at least one notch 50, to anchor the slide piece 10 with base piece 5 to form the medical device management unit 1 in locked position. In order to create a solid anchoring of the locking means 30 within the channel 40, the locking means 30 and the channel 40 should have a size ratio that allows them to be in continual contact with one another at each of their surfaces. Further, the size ratio enables the engagement and the release of locking means 30 with or from the channel 40 occur with ease. The anchoring of more than one of the at least one protrusion 45 within more than one of the at least one notch 50 may produce a series of clicks that may be felt and/or heard, notifying the user that the medical device 65 has been secured within the medical device management unit 1.

Figure 6:
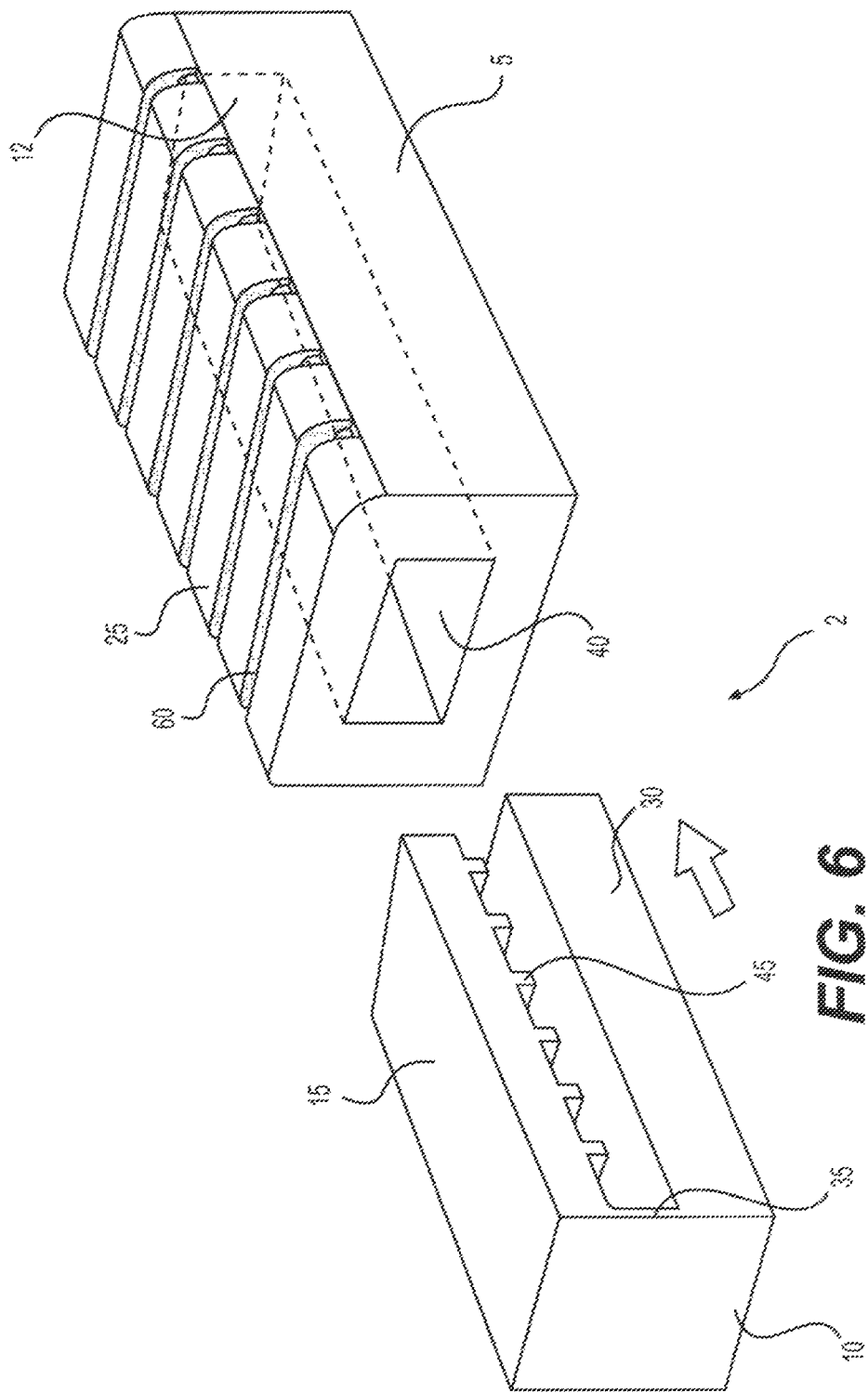
FIG. 6 is an exploded side view of an alternative embodiment of the medical device management unit of the present invention.

FIG. 6 depicts a second embodiment of the invention to manage medical device 65, wherein the medical device management unit 2 has a base piece 5 and a slide piece 10. Specifically, the one or more medical device 65 is placed within a trench 60, which extends across the surface means 25 and perpendicular to the channel 40, to form a pathway for the medical device 65. Surface means 25 may be flat or dome shaped. The locking means 30 then engages the channel 40, such that the movement of the locking means 30, and the connecting means 35, induces the cover means 15 to cover the surface means 25. The movement of the locking means 30 and the cover means 25 may occur simultaneously or sequentially with minimal delay. In this embodiment, the cover means 15 further comprises at least one protrusion 45, which engages the trench 60 to compartmentalize the pathway that contains the medical device 65, and thus secures the at least one medical device 65 within medical management unit 2. Additionally, the engagement of the at least one protrusion 45 and at least one trench 60 may produce a series of clicks that are felt and/or heard to notify the user that a portion of the one or more medical device 65 has been secured.

Figure 1:
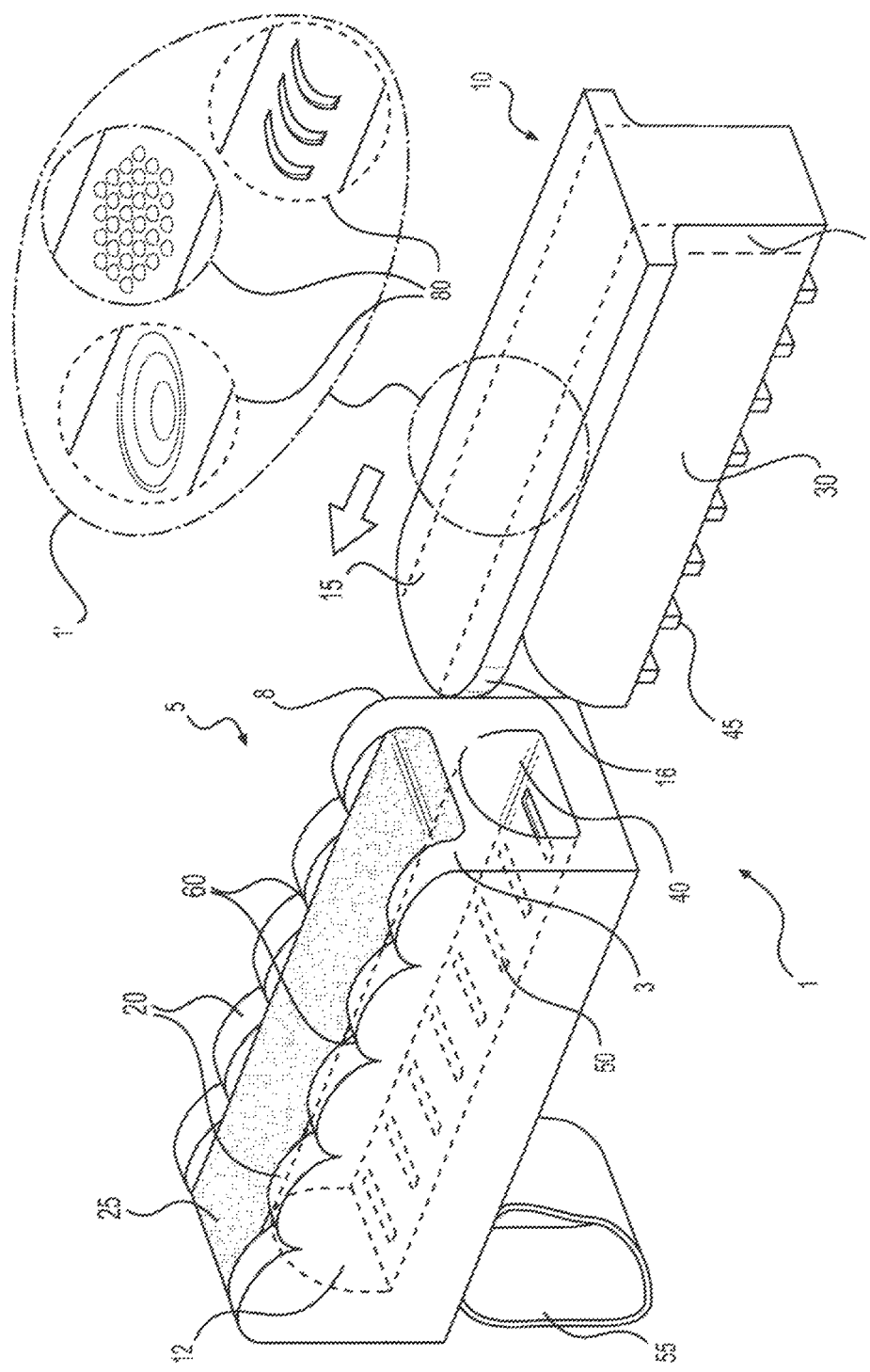
FIG. 1 is an exploded side view of a medical device management unit according to an embodiment of the present invention.

The channel 40 of medical device management unit 1 and 2 is parallel to first side 3 and opposing second side 8 of the surface means 25, and either only open on one end, or open at both ends as demonstrated by open channel side 12 of channel 40 in FIGS. 1 and 6. The open ends allow a user to release the slide piece 10 from base piece 5 with ease, because the locking means 30 can be pushed from the opposite side of the channel 40 from which it was inserted. Further, FIG. 1' shows various embodiments of a gripping means 80 that aids a user in locking or releasing slide piece 10 into or from base piece 5. The gripping means 80 may comprise various shapes and/or patterns, including raised or indented swirl patterns, a series of protrusions, or a raised wave pattern. Further, the gripping means 80 may be made from a sticky material, elastomeric material, rough material, or other materials that are useful for maintaining a user's grip for the user to either engage the locking means 30 with the channel 40, or release the locking means 30 from the channel 40.

The cover means 15 of the medical device management unit 1 either covers the central portion of the surface means 25 alone, or the support means 20 in addition to the central portion of the surface means 25. In the case that the cover means 15 covers the central portion of the surface means 25 alone, at least one trench 60 on the first side 3 captures the medical device 65 and directs the medical device 65 towards another trench 60 on the opposing second side 8, to form a pathway on which the medical device is organized and managed on the surface means 25. Then, the cover means 15 presses the medical device 65, in its pathway, onto the central portion of the surface means 25, wherein the central portion is made of a cushioning material such as silicone. The pressing motion secures the medical device 65 onto the surface means 25, yet still allows capture and release of the medical device 65. Further, the cover means 15 may have rounded edges, which catch less readily and reduce friction on the central portion of the surface means 25, or on the support means 20 as the slide piece 10 is repeatedly locked or released from base piece 5 to manage and organize the medical device 65.

In the embodiment where the cover means covers both the central portion of the surface means 25 and the support means 20, the cover means 15 is elevated above the surface means 25 to form a space, such that at least one trench 60 on the first side 3 captures the medical device 65 and directs the medical device 65 towards at least one trench 60 on the opposing second side 8, to form a pathway on which the medical device is organized and managed on the surface means 25. This space, measured as the height of the support means 20 above the surface means 25, is preferably between 0-2 mm, but may be larger so as to accommodate medical devices 65 of various diameter and size.

Figure 3:
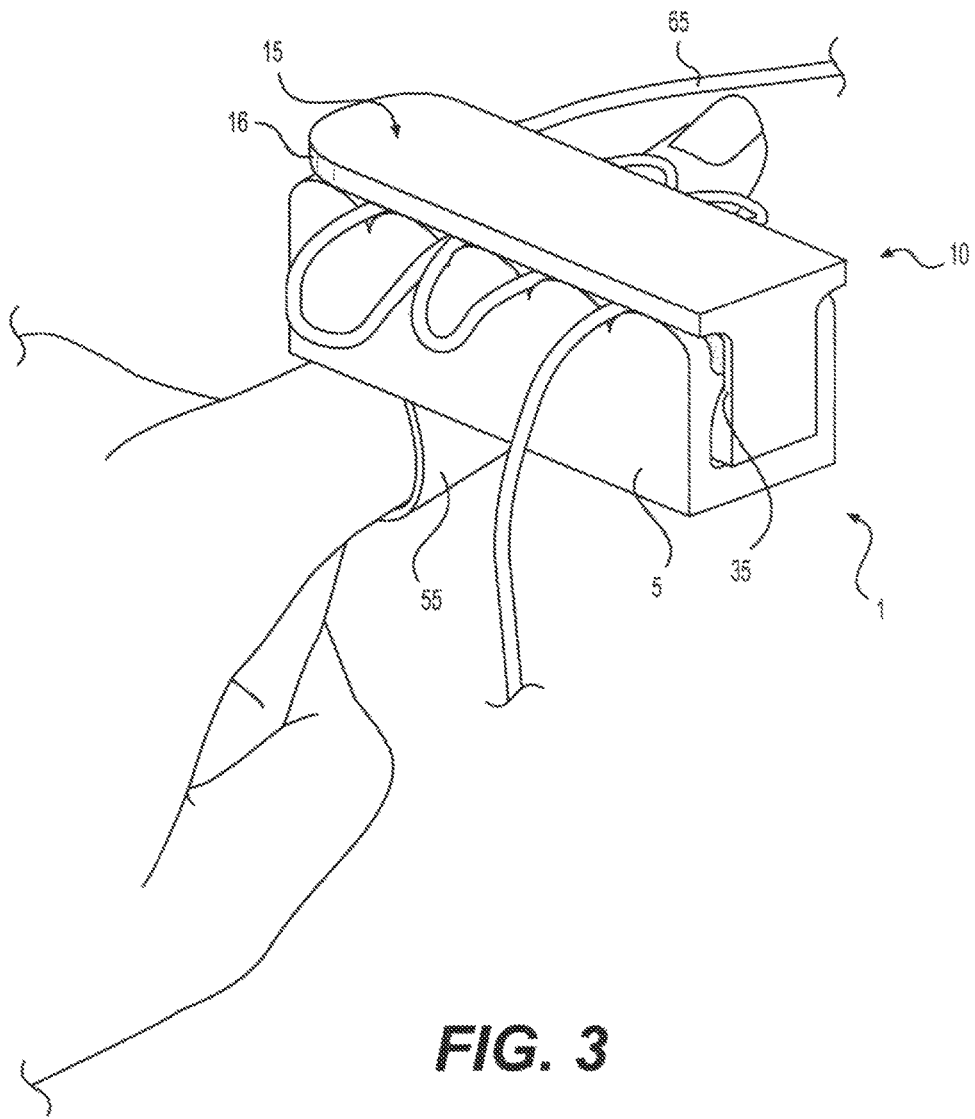
FIG. 3 depicts a side view of the medical device management unit of the present invention as it would be used during a medical procedure, with a finger inserted through the attached finger loop, and a medical cord looped through the device for sequential capture.
Figure 4:
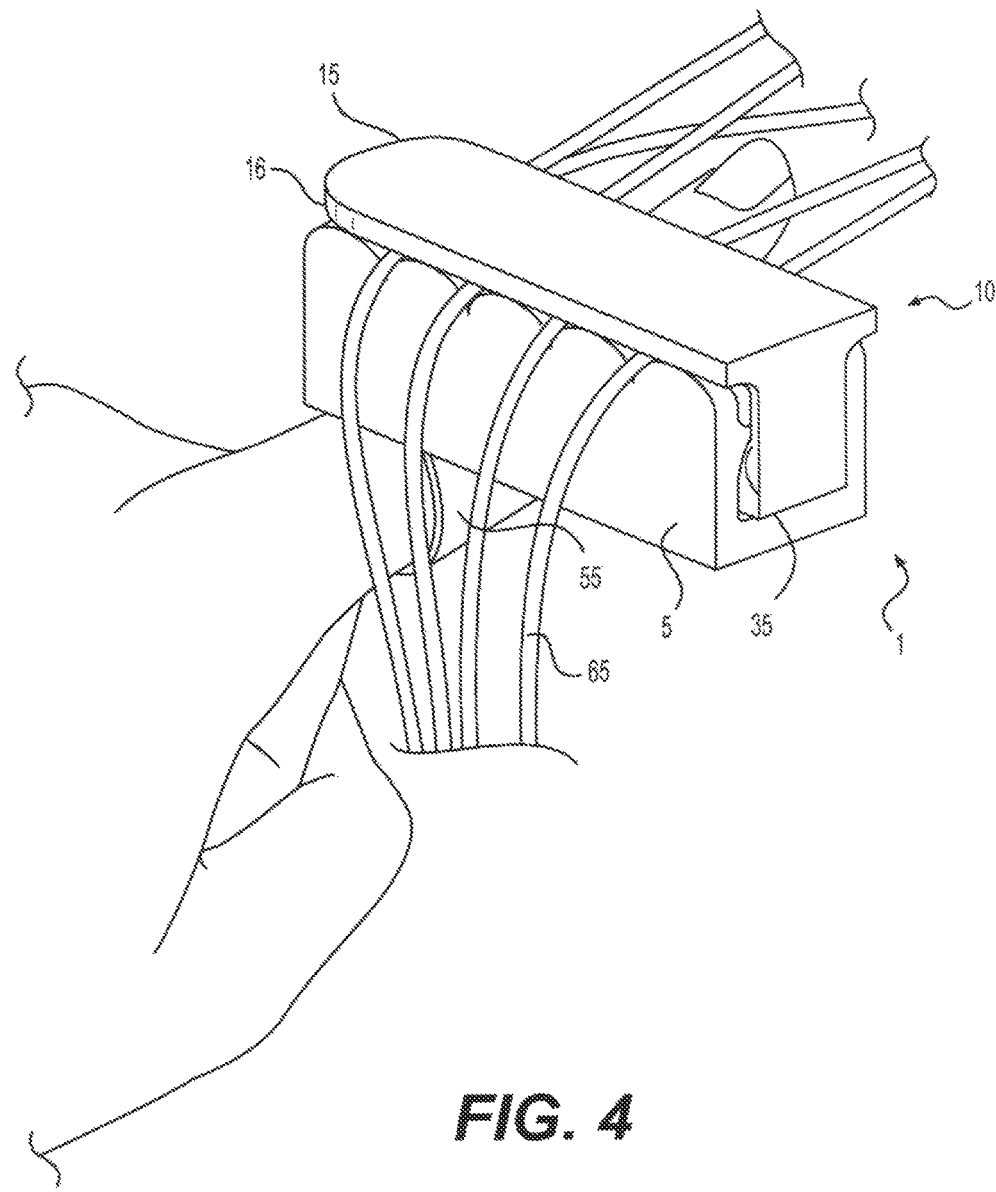
FIG. 4 depicts a side view of the medical device management unit of the present invention as it would be used during a surgical operation, with a finger inserted through the attached finger loop, and multiple medical cords threaded through the medical device management pathways of the unit.
Figure 5:
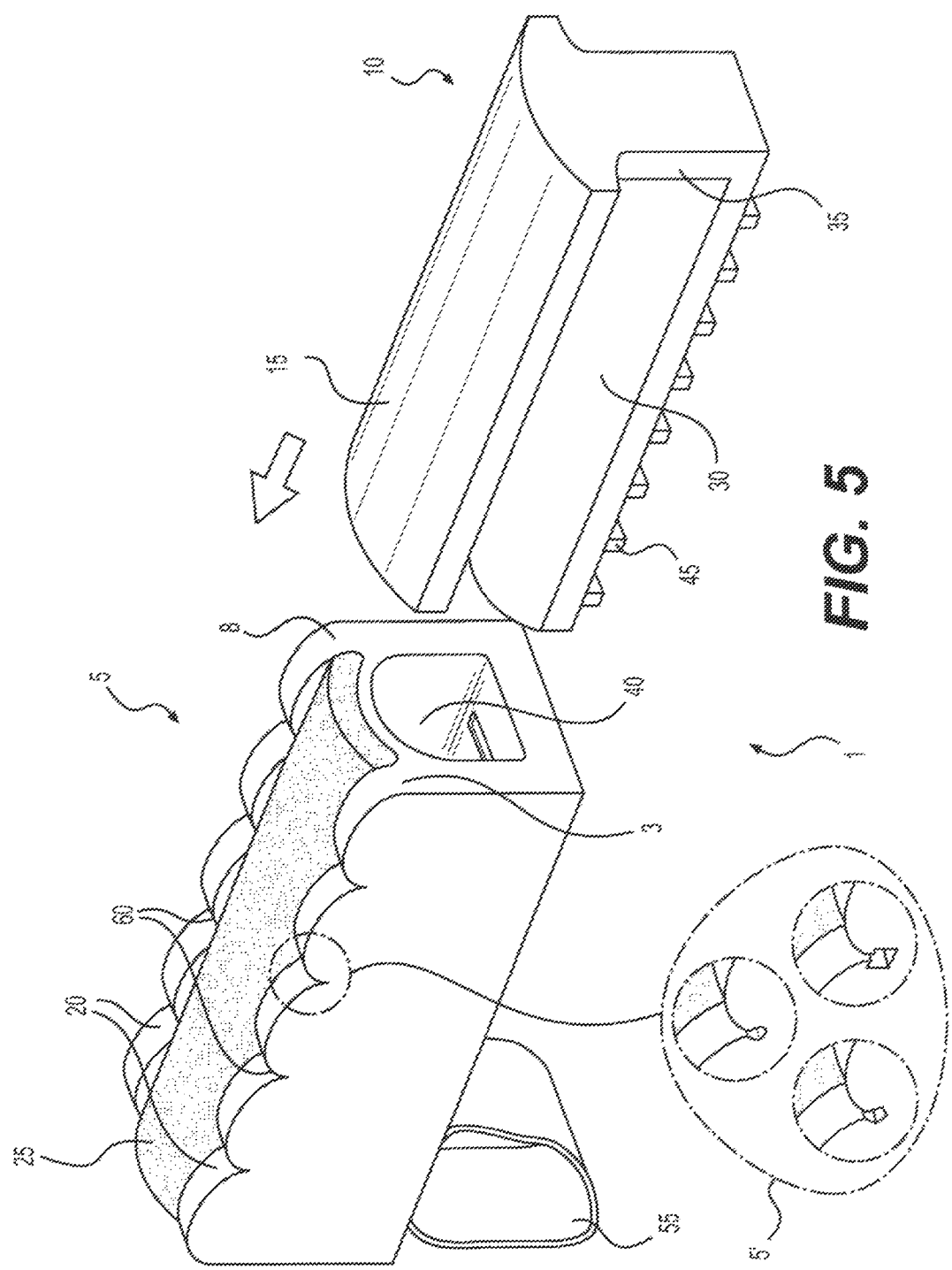
FIG. 5 is an exploded side view of a medical device management unit according to an embodiment of the present invention.

The height of the support means 20 can be modified relative to the central portion of the surface means 25 to accommodate and to secure medical devices 65 of various shapes and sizes within the medical device management unit 1. Various trench 60 shapes may be utilized to accommodate medical devices 65 of various shapes and sizes. As shown in FIG. 5', rather than the undulating curvature of the support means 20 which defines the trenches 60 as depicted in FIGS. 1, 2A, 2B, 3, and 4, the trenches 60 may be defined by a support means 20 that comprises a series of surface undulations defining one or more geometric patterns including diamond, teardrop, or square. The angle of the support means 20 boundaries that define the trenches 60 may also be modified to properly accommodate the medical device 65 that is to be managed by the medical device management unit 1.

FIGS. 7 through 11 depict a third embodiment of the invention for managing medical device 65, wherein the medical device management unit 90 includes a base piece 95 that has a housing 96 with an opening 132, sides 97 and an extended portion 93, and a surface means 100. Unit 90 further comprises a slide piece 130 that has a gripping means 125 in the form of a raise swirl pattern, an indented swirl pattern, a series of protrusions, and a raised wave pattern. The slide piece 130 may have a flange 117, which extends along and parallels with each side 136 of the slide piece 130. One or more medical device 65 may be organized and managed by placing medical device 65 onto a pathway on the surface means 100 as defined by trenches 112 that are formed by protrusions 110 along the length of the surface means 100. The slide piece 130 then slides over and covers surface means 100 and locks medical device 65 onto the surface means 100. The contact surfaces of surface means 100 with the slide piece 130 are preferably flat, dome-shaped, or of any other shape that facilitates the organization of medical device 65. An anchoring means 135 and 138 in the form of anchoring tabs located on one end 133 of the slide piece 130 engages capture means 120 in the form of a safety track located within housing 96, such that the engagement retains the slide piece 130 partially or completely within housing 96. When a user pushes gripping means 125 atop of the slide piece 130 to move slide piece 130, optionally creating an "audible click", the movement induces anchoring means 135 and 138 to pass through each increment of the safety track 120, flex and allow slide piece 130 to slide over surface means 100, such that the flange 117 of slide piece 130 fits into guiding means 114 in the form of grooves located within protrusion 110, which slides the slide piece 130 to stably cover surface means 100. The surface means 100 is either enclosed or part of the extending end 93. If enclosed, surface means 100 is optionally secured by secure means 115 in the form of pins or surface protrusions from the interior of housing 96 and resting means 113 in the form of rails within extending end 93 to be stationary within the extended end 93, while protrusions 110 extend from sides 141 and 142 of extending end 93, and above each side of surface means 100 forming trenches 112. The protrusions may be further fortified or strengthened by ribs 116 that correspond to the protrusion 110 and extends to the bottom of extending end 93. Surface means 100 may have an irregular end 111 that anchors or secures surface means 100 within housing 96. The entire base piece 95 may be in the form of a shell that is formed from halved parts secured via holding means 140 and 145. The base piece 95 further includes a barrier end 105 that retains slide piece 130 within base piece 95. Base piece 95 optionally includes tunnel 122 on each side 97 for accommodating flange 117 extending from each side of slide piece 130.

As shown in FIG. 1, the surface means 25 has a portion that is preferably made from an elastomeric material. Specifically, the elastomeric material is located throughout the central portion of the surface means 25. Alternatively as shown in FIG. 6, the elastomeric material is located at the base of the trench 60. The elastomeric material is selected from the group consisting of silicone, foam, natural rubber, manufactured rubber, recycled rubber, gels, glues, beads, and encapsulated viscous materials, each of which may be appropriate depending on the degree to which the medical device being managed needs to be secured. Preferably, the elastomeric material is silicone.

Figure 7:
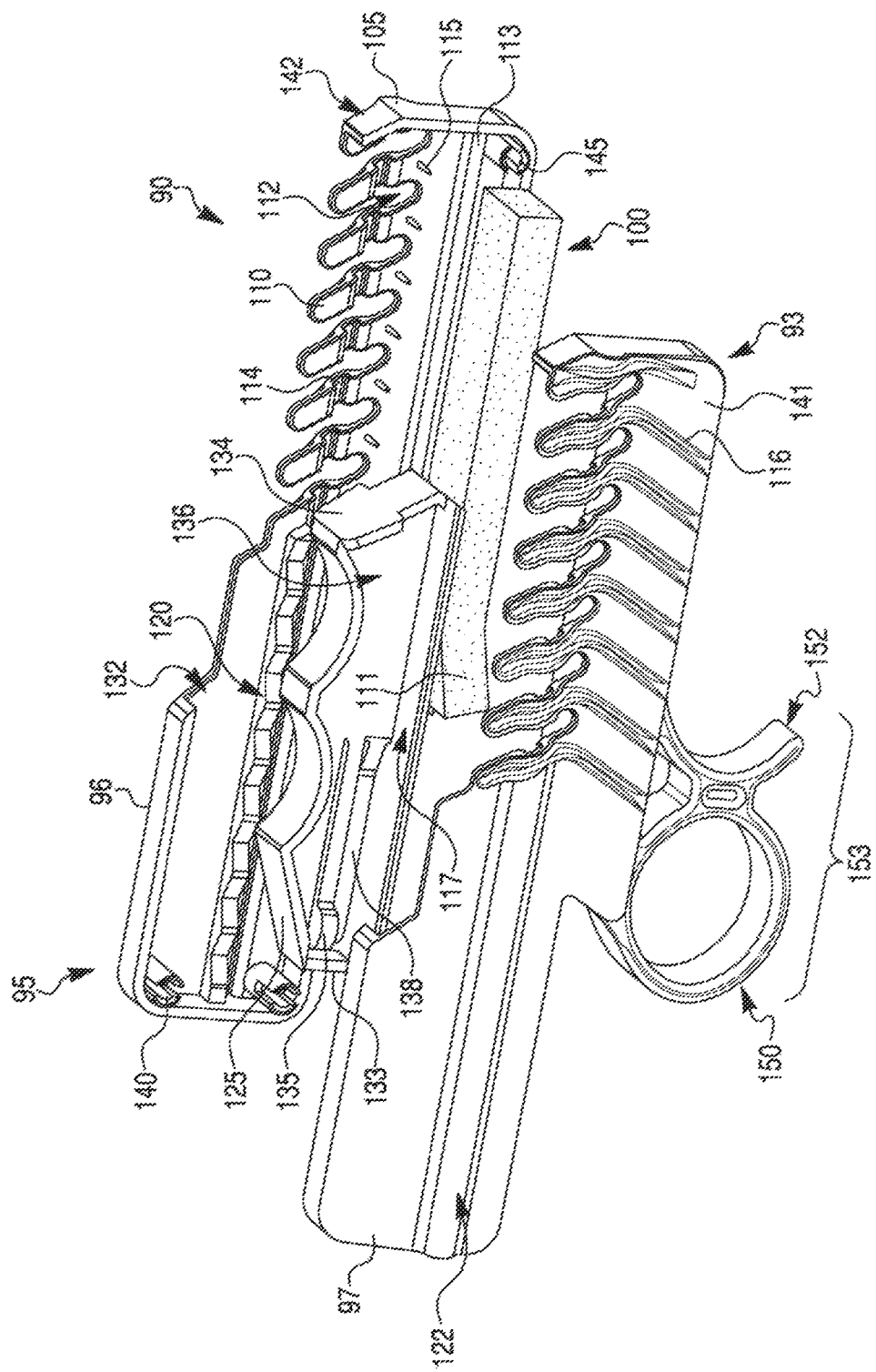
FIG. 7 depicts an exploded side view of an alternative embodiment of the medical device management unit of the present invention.

Alternatively, as shown in FIG. 7, surface means 100 is enclosed within the extended end 93 of base 95, and has a portion or is entirely made from the elastomeric material.

In other embodiments an antiseptic may be applied to at least a portion of the pathway formed by at least one trench 60 (as shown in FIG. 6, dotted surface within trench 60) or surface means 100 as shown in FIG. 7, for managing and maintaining sterility of at least one medical device 65. This coating may be applied during or after the manufacture of the medical device management units 1, 2 or 90, and the device may be packaged and/or sold with the pre-applied antiseptic coating. The antiseptic coating may be applied to any portion of the surface means and/or the underside of the cover means 15. It is preferable that the antiseptic be applied to each trench 60 or surface means 100, such that the medical device 65 will maintain contact with the coating during its management. Alternatively, the whole device is sterilized by a gas such as ethylene oxide.

Figure 2A:
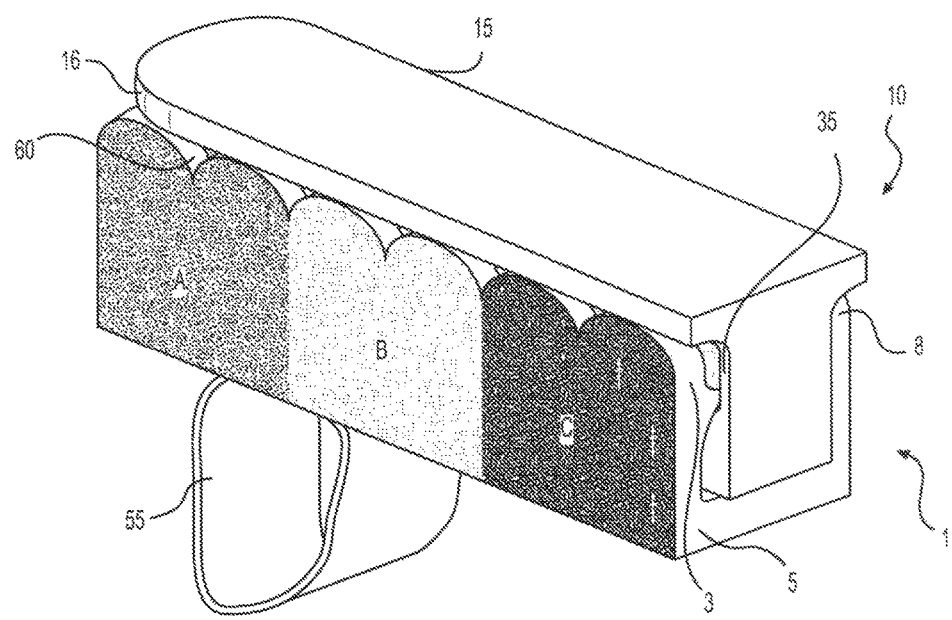
FIG. 2A is a side view of a medical device management unit according to an embodiment of the present invention while in a "locked" position.
Figure 2B:
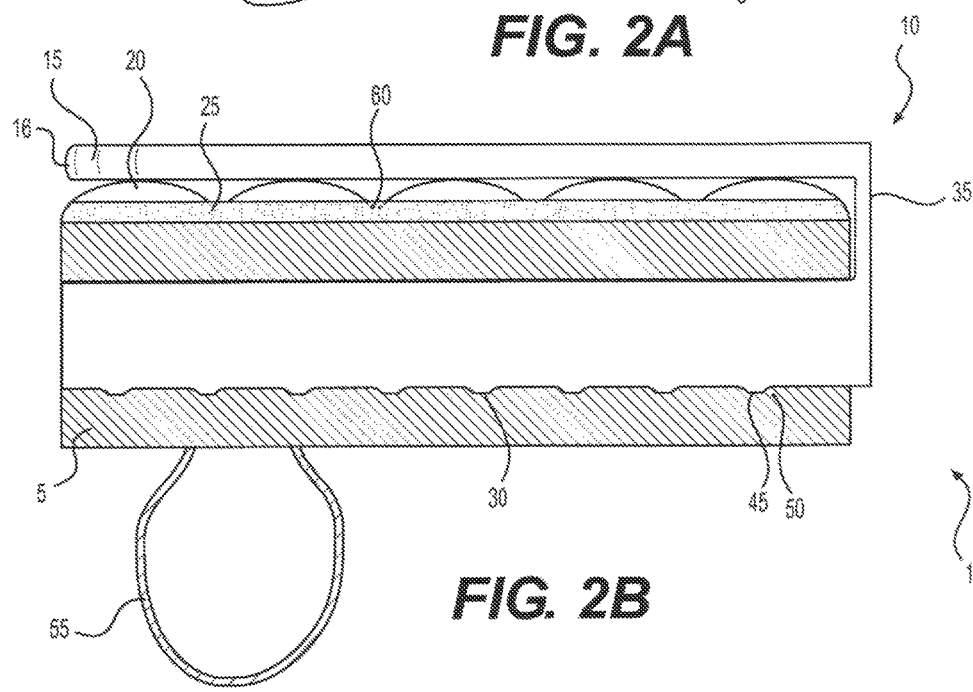
FIG. 2B is a cross section of the medical device management unit of the present invention while in the "locked" position.

As shown in FIG. 2A the medical device management unit 1 may contain an identification system to identify the various medical devices 65 that are located and organized within the medical device management unit 1. The identification system may be in the form of colors, indicia or composite thereof located near the trench 60 and visible to the user while the unit is in use, or only become visible when a medical device is placed and secured within the management unit 1, to display "real time" identification. The indicia are markings that include letters, numbers, symbols, and patterns.

Each of the embodiments of the current invention may include an optional finger loop 55. This feature allows the user to maintain control over the medical device management unit 1 or 2, as well as "flip" the device onto the back of the hand when the device is not in use, as with wearing a ring, freeing the hand for other tasks. The finger loop 55 may be attached to the base piece 5 or the slide piece 10. FIGS. 3 and 4 show the finger loop 55 as it would be worn by an assistant or physician during the course of a medical procedure. The finger loop 55 may be made of an elastic material or contain a tightening and loosening mechanism such that it may be worn by individuals having different sized fingers.

In the case of device 90, a hand held portion 153 comprises a thumb loop 150 and finger resting portion 152, to enable the user to hold device 100 using one hand, while holding the gripping means 125 atop of the slide piece 130 with the other hand to control the movement of the slide piece 130. Alternatively, the device is preferably controlled entirely by one hand. Any finger except for the thumb is inserted into loop 150, and the thumb moves the gripping means 125. The user's palm wraps around housing 96, leaving the other hand to wind catheters or wires around device 90.

In addition to more traditional manufacturing processes such as molding, metal welding, or ultrasound welding, medical device management unit 1 and 90 may be manufactured in whole or in part by a 3D printer. The base piece 5 and the slide piece 10, and alternatively, base piece 95 and slide piece 130 may also be sold as a prepackaged kit along with at least one medical device 65.

The components of the base piece 5 and the slide piece 10, or base piece 95 and slide piece 130 may be made of the same material or they may be made of different materials. Examples of materials that can be utilized for these components include: metals, ceramics, plastics, hardened rubbers, wood, hardened glass, carbon fiber, paper composite and mixtures thereof. The materials utilized are preferably durable and sterilizable so as to accommodate multiple uses over the course of more than one medical procedure.

The dimension of the medical device management unit 1 or 90 is such that when the slide piece is incorporated with the base piece to form the management unit in "locked" mode, the locked management unit has a length of no more than 20 cm, and no less than 4 cm; a width that is no more than 7 cm and no less than 1.0 cm; and a height of no more than 10 cm and no less than 1 cm. Further, the width of the surface means 25 or 100, that is, from the edge of first side 3 to the edge of opposing side 8 is preferably no less than 0.5 cm and no more than 7 cm; and the length of the surface means 25 or 100 is preferably no less than 4 cm and no more than 15 cm. Correspondingly, the width of the cover means 15 is preferably no less than 1.5 cm and no more than 7 cm, such that it covers each of the trenches 60; and the length of the cover means 15 or slide piece 130 is preferably no less than 4 cm and no more than 20 cm such that the cover means 15 or slide piece 130 covers a portion of the center of the surface means 25 or 100, and may cover a portion of the support means 20 or protrusion 110. The length of the channel 40, if present, is corresponding to the length of the locking means 30, preferably run the length of the surface means 25 and the cover means 15, that is, the length of the channel 40 and the length of the locking means 30 are each preferably no less than 4 cm and no more than 15 cm. However, the length of the channel 40, and correspondingly the length of the locking means 30 may be shorter than the length of the surface means 25 and the cover means 15.

The trenches are located on the same side 3 or 8 of unit 1, or on side 141 or 142 of unit 90. Alternatively, the trenches 60 or 112 extend across the surface means 25 or 100, wherein the trenches are spaced at least 0.25 cm apart and at most 7 cm apart.

With regard to medical device management unit 1 or 90, it is preferable that where a malleable material such as silicone is utilized for the surface means 25 or 100, that it has a depth equal to at least that of the circumference of the medical device 65 that is being managed during the procedure. Similarly, the trenches 60 of medical device management unit 1 and 3, and trenches 112 of unit 90 preferably comprise depths at least equal to the circumference of the medical device 65 that is being managed during the procedure.

For medical device management unit 1, the notches 50 are preferably as deep as the length of the protrusions 45 such that the locking piece 30 is flush with the channel 40 when the medical device unit 1 is "locked." The preferred depth of the notches 50, and therefore the corresponding preferred length of the protrusions 45 is no less than 3 mm and no more than 8 mm.

The protrusions 45 of medical device management unit 2 preferably project out from the cover means 15 no further than the depth of trenches 60, the depth and projection length being dependent on the circumference of the medical device 65 that is being managed during the procedure.

Embodiments of the invention not meant for handheld use may have dimensions larger than the preferred dimensions to accommodate larger medical devices 65 or a number of medical devices 65 simultaneously.

Method of Operation

The user may utilize the medical device management unit in various ways depending on the medical procedure being performed and the medical device(s) required to perform the medical procedure. If the goal is to sequentially capture or release a single medical device 65 as in FIG. 3, the medical device management unit 1 will be laid open such that the surface means 25 and support means 20 are uncovered. The medical device 65 is then laid in a first trench 60 on first side 3, which directs a pathway for medical device 65 to be threaded over the surface means 25 and through the corresponding trench 60 on the opposite second side 8 of the surface means 25. This procedure is repeated in the opposite direction until the desired number of loops have been created for maintaining control of the medical device 65. With the medical device 65 looped on the surface means 25, the user then takes the slide piece 10, inserts and anchors the locking means 30 into the channel 40. The user may place her thumb or a different finger on the gripping means 80 on cover means 15 to aid in the insertion of the locking means 30 into the channel 40. The engagement of the locking means 30 within the channel 40 may simultaneously or consequently enable the cover means 15 to cover the surface means 25 through connecting means 35, thereby containing the medical device 65 in the desired looped fashion as shown in FIG. 3.

As the locking means 30 enters and engages channel 40, at least one the protrusion 45 that are located at the underside of the locking means 30, engages at least one notch 50 of the base piece 5 to anchor the slide piece 10 within base piece 5. The anchoring may produce an audible click to notify the user that a portion of the medical device has been secured. The user may then optionally place one of her fingers through the finger loop 55 for additional control of the medical device management unit 1. The finger loop 55 also allows the user to "flip" the medical device unit 1 onto the back of her hand when it is not in use. To open the medical device management unit 1 for reloading or sterilization the user may 1) push the locking means 30 out of channel 40 from the opposing channel side 12 of base piece 5 or 2) pull the slide piece 10 by connecting means 35 and the base piece 5 in opposite directions. The gripping means 80 is also useful during this process as it allows additional control over the slide piece 10.

If medical device management unit 2 is used for sequentially capturing or releasing a single medical device 65, the procedure implemented is similar to using medical device management unit 1.

The user takes the medical device 65 and lays it in a first trench 60 that expands across the surface means 25 to form a pathway on the base piece 5. The medical device 65 is then looped into the next sequential trench 60 and this procedure is repeated from one side of the surface means to the other, until the desired number of loops has been created and/or all of the trenches 60 have been filled. The user then takes the slide piece 10 and engages the locking means 30 within the channel 40. Since the locking means 30 and the cover means 15 are connected via the connecting means 35, the engagement of the locking means 30 and channel 40 enables the cover means 15 to simultaneously or consequentially cover the surface means 25 with minimal delay. As locking means 30 enters channel 40, the protrusions 45 located under the cover means 15 engage and are anchored by the trench 60, such that the medical device 65 is compartmentalized and secured within the trench 60. The engagement may also produce at least one audible click to notify the user that a portion of the medical device has been secured. The finger loop 55 may be utilized in the same manner for medical device management unit 2 as for medical device management unit 1. To open medical device unit 2 for reloading or sterilization the user may push the end of the locking means 30 from opposing channel side 12, while simultaneously pulling the base piece 5 in the opposite direction of the slide piece 10. The gripping means 80 may also be utilized to help move the cover means 15 back over the surface means 25.

Figure 10:
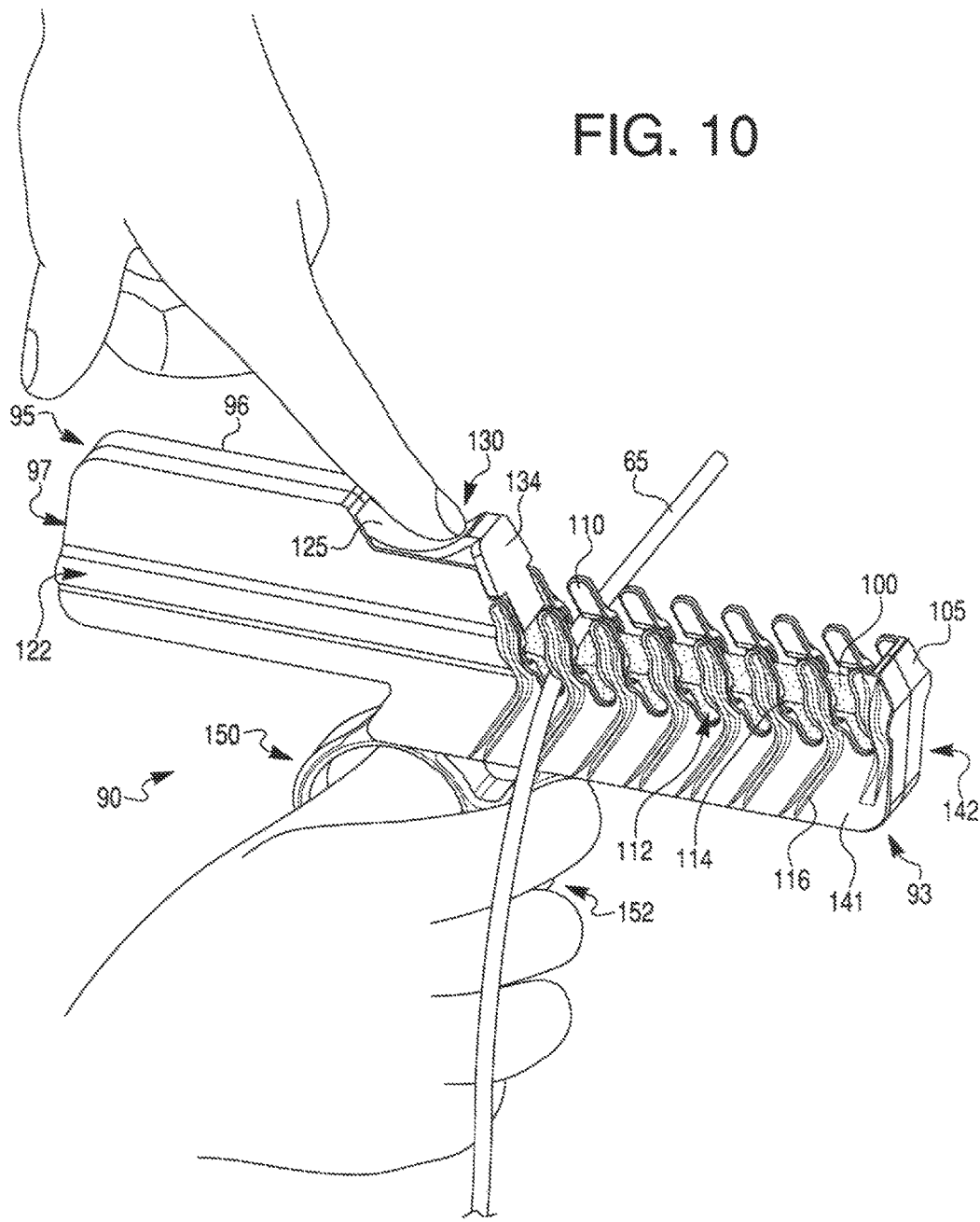
FIG. 10 depicts a side view of an alternative embodiment of the medical device management unit as it would be used during a medical procedure, with a medical cord inserted onto the surface means of the medical device management unit.

If medical device management unit 90 is used for sequentially capturing or releasing a single medical device 65, the procedure implemented is shown in FIG. 10, wherein the user holds unit 90 by 150 and 152, the medical device management unit 90 is laid open such that the slide piece 130 is retracted within housing 96, and surface means 100 is exposed. The medical device 65 is laid in a first trench 112 on first side 141 of extending end 93, which directs a pathway for medical device 65 to be threaded over the surface means 100 and through the corresponding trench 112 on the opposite second side 142 of the extending end 93. This procedure is repeated until the desired number of loops has been created for maintaining control of the medical device 65. With the medical device 65 looped on the surface means 100, the user then uses the other hand to exert force on gripping means 125 to release the slide piece 130, by dislodging anchoring means 135 and 138 from capture means safety track 120 (not shown) and slides the slide piece 130 onto surface means 100. When the user stops the slide piece 130, anchor means 135 and 138 engage capture means safety track 120 and lock slide piece 130, thereby forming a "locked" position as shown in FIG. 11.

Figure 11:
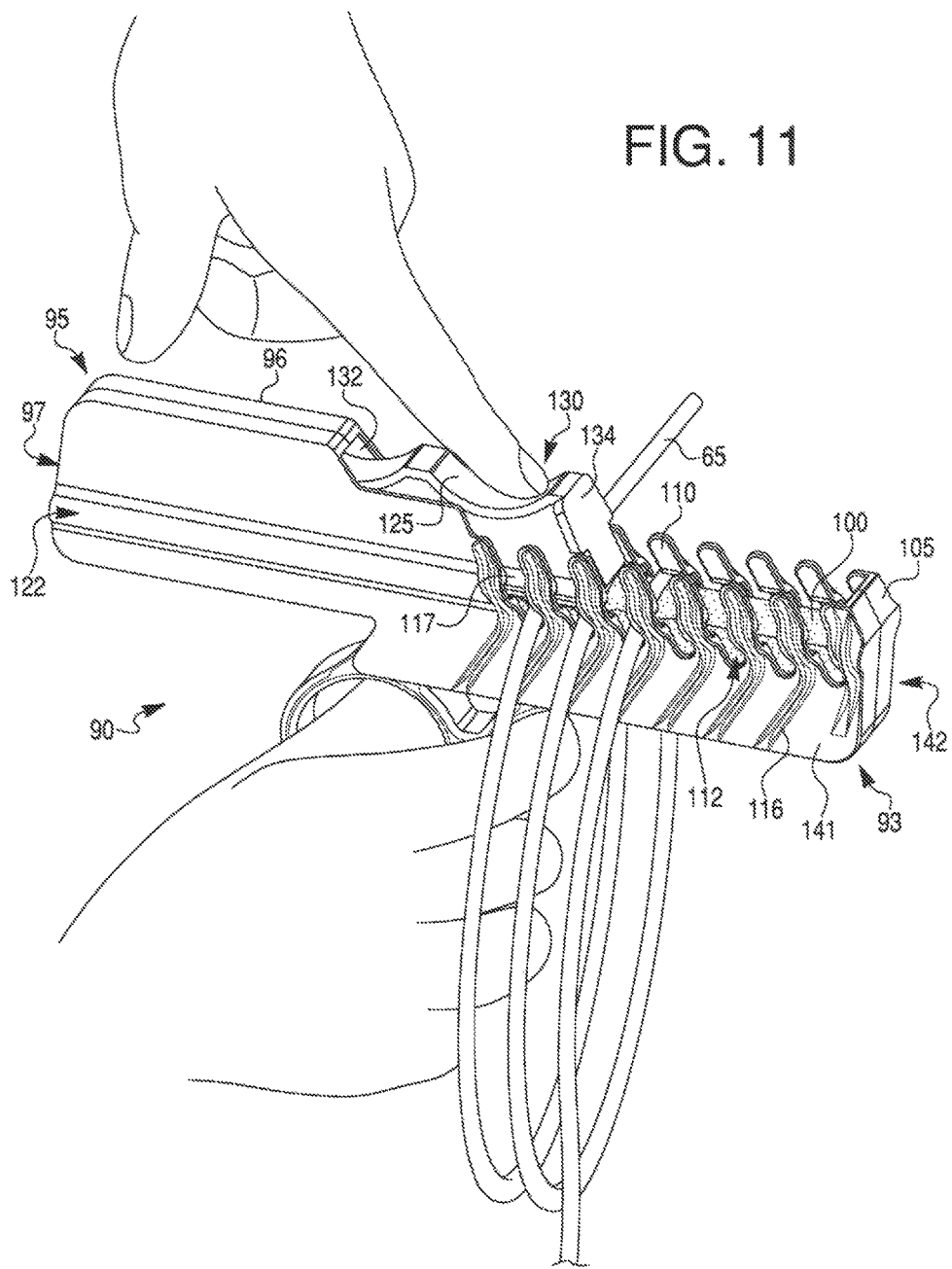
FIG. 11 depicts an alternative embodiment of the medical device management unit holding multiple loops of the medical cord, such that the slide piece covers and secures the cord onto the surface means in a "semi-closed" position.

In an alternative procedure not shown in FIGS. 10 and 11, the user manipulates device 90 using entirely one hand. Specifically, the user loops a finger into 150 and holding 152 in one hand, and uses the thumb of the same hand to pull back on gripping means 125 to retract slide piece 130 into housing 96 to expose surface means 100, and to open the medical device management unit 90 for reloading or sterilization.

The user then uses a second hand to lay the medical device 65 in a first trench 112 on first side 141 of extending end 93, which directs a pathway for medical device 65 to be threaded over the surface means 100 and through the corresponding trench 112 on the opposite second side 142 of the extending end 93. This procedure is repeated until the desired number of loops has been created for maintaining control of the medical device 65.

With the medical device 65 looped on the surface means 100, the user then again uses the thumb to exert force on gripping means 125 to release the slide piece 130, by dislodging anchoring means 135 and 138 from capture means safety track 120 (not shown) and slides the slide piece 130 onto surface means 100. When the user stops the slide piece 130, anchor means 135 and 138 engage capture means safety track 120 and lock slide piece 130, thereby forming a "locked" position as shown in FIG. 11.

The invention claimed is:

1. A handheld medical device management unit comprising a base piece and a solid slide piece, wherein said base piece comprising 1) one flat elastomeric surface means located between the top of said base piece and said solid slide piece, for resting at least one medical device selected from the group consisting of cables, sutures, catheters, balloons, rods, and guide wires; 2) a plurality of trenches located solely on the peripheral edge of said base piece, and spaced along the length of said one flat elastomeric surface means; and 3) at least one pathway on said one flat elastomeric surface means solely formed by said plurality of trenches and at least one said medical device, such that said solid slide piece is operatively slideable in a linear direction from a first end of said one flat elastomeric surface means to an opposing second end of said one flat elastomeric surface means, to expose said one flat elastomeric surface means for placement of at least said medical device within said at least one pathway, and to cover and adjacent to said one flat elastomeric surface means to secure and render immobile at least one said medical device within said at least one pathway, wherein a hand-holding portion extended from the underside of said handheld medical device management unit.

2. The medical device management unit of claim 1, wherein said base piece further includes a capture means, and said slide piece further includes at least one anchoring means that engages said capture means to secure said solid slide piece with said base piece.

3. The medical device management unit of claim 2, wherein said capture means is a safety track, and said at least one anchoring means is an anchoring tab.

4. The medical device management unit of claim 3, wherein said at least one anchoring means is flexible to be moved along said capture means and engages said capture means to secure said solid slide piece when said solid slide piece is still.

5. The medical device management unit of claim 1, wherein said base piece further comprises a first end and a second opposing end that comprises a first side and a second opposing side.

6. The medical device management unit of claim 5, wherein a plurality of protrusions extend from said first and said second opposing end, and raises above said one flat elastomeric surface means to form said trenches.

7. The medical device management unit of claim 6, wherein said protrusions further include a guiding means that guides and secures said solid slide piece to slide over said one flat elastomeric surface means.

8. The medical device management unit of claim 7, wherein said guiding means are grooves in parallel with sides of said solid slide piece.

9. The medical device management unit of claim 8, wherein a flange extends from said each side of said solid slide piece and said flange fits into said guiding means to stably hold said solid slide piece over said one flat elastomeric surface means.

10. The medical device management unit of claim 5, wherein said one flat elastomeric surface means is either enclosed or part of said second opposing end of said base piece.

11. The medical device management unit of claim 5, wherein said first end of said base piece holds said solid slide piece in a housing that opens towards said one flat elastomeric surface means.

12. The medical device management unit of claim 1, wherein a portion of said one flat elastomeric surface means or the base of said plurality of trenches is selected from the group consisting of: silicone, foam, natural rubber, manufactured rubber, recycled rubber, gels, glues, beads, and encapsulate viscous fluids.

13. The medical device management unit of claim 1, wherein said management unit has a length of no more than 20 cm, and no less than 4 cm; a width that is no more than 7 cm and no less than 0.5 cm; and a height of no more than 10 cm and no less than 1 cm.

14. The medical device management unit of claim 1, wherein said solid slide piece further includes a gripping means selected from a raised pattern, an indented pattern, and combination thereof.

15. The medical device management unit of claim 1, wherein said management unit further includes an identification system selected from the group consisting of colors, indicia and composite thereof.

16. The medical device management unit of claim 1, wherein said at least one pathway and/or trench is coated with an antiseptic, or said device is sterilized by gas.

17. The medical device management unit of claim 6, wherein said base piece further includes a fortifying rib that corresponds and is adjacent to said each protrusion, and extends towards the bottom of said second opposing end.

18. A method for managing a medical device comprising:
a) holding a handheld medical device management unit by hand or fingers holding onto a hand-holding portion extended from the underside of said unit;
b) holding a solid slide piece on a first end of one flat elastomeric surface means of a base piece of a medical device management unit, such that said flat elastomeric surface means is located between the top of said base piece and said solid slide piece, to expose said one flat elastomeric surface means for placement of at least one medical device selected from the group consisting of cables, sutures, catheters, balloons, rods, and guide wires thereon, wherein that at least one medical device pathway is formed by 1) at least one said medical device; and 2) a plurality of trenches located solely on the peripheral edge of said base piece and spaced along the length of said one flat elastomeric surface means of a base piece of a medical device management unit in a linear direction;
c) sliding said solid slide piece to cover and adjacent to said one flat elastomeric surface means; and
d) securing and rendering immobile said at least one medical device within said pathway.

19. The method according to claim 18, wherein said method further includes step b2) moving said solid sliding piece to flex at least on anchoring means of said solid slide piece over a capture means of said base piece, to release said solid sliding piece from said base piece.

20. The method according to claim 19, wherein said method further includes step c2) stopping said solid slide piece, and said capture means of said base piece engaging said at least one anchoring means of said solid slide piece to secure said slide piece over said one flat elastomeric surface means.

21. The method according to claim 19, wherein said anchoring means is an anchoring tab and said capture means is a safety track.

22. The method according to claim 20, wherein said d) produces an audible or felt notification to user to inform said user that said medical device is secured within said management unit.

* * * * *